United States Patent
Sukata et al.

[11] Patent Number: 5,990,332
[45] Date of Patent: Nov. 23, 1999

[54] METAL COMPOUND OF AROMATIC HYDROXYCARBOXYLIC ACID, CHARGE CONTROL AGENT, TONER, AND POWDERY PAINT

[75] Inventors: Kazuaki Sukata, Kyoto; Tohru Tsuruhara, Osaka; Shun-Ichiro Yamanaka, Osaka; Shuji Sugawara, Osaka; Masashi Yasumatsu, Osaka, all of Japan

[73] Assignee: Orient Chemical Industries, Ltd., Osaka, Japan

[21] Appl. No.: 09/217,269

[22] Filed: Dec. 21, 1998

Related U.S. Application Data

[62] Division of application No. 08/703,821, Aug. 27, 1996.

[30] Foreign Application Priority Data

Aug. 29, 1995 [JP] Japan .................. 7-245564
Mar. 7, 1996 [JP] Japan .................. 8-80953

[51] Int. Cl.⁶ .......................... C07F 19/00; C07F 15/00; C07F 7/28
[52] U.S. Cl. .......................... 556/49; 556/55; 556/106; 556/108; 556/150; 556/184; 556/437; 556/443; 252/182.11; 430/110
[58] Field of Search .................. 556/49, 55, 106, 556/108, 150, 184, 437, 443; 252/182.11

[56] References Cited

PUBLICATIONS

Chemical Abstracts, vol. 99, No. 23, abstract No. 194629z, Klasek et al., CS 194,148 (Cl. C07C65/12) Mar. 30, 1982, Dec. 5, 1983.

*Primary Examiner*—Porfirio Nazario-Gonzalez
*Attorney, Agent, or Firm*—McGlew and Tuttle, P.C.

[57] ABSTRACT

Metal compound of formula [I] which is excellent in charge control or charge-enhancing property, and toner for developing electrostatic images and powdery paint for electrostatic painting incorporating thereof:

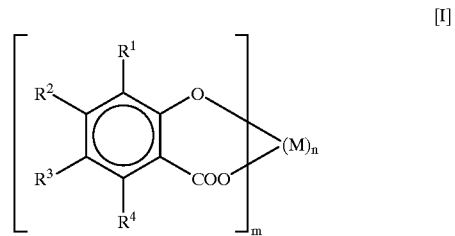

wherein $R^1$, $R^2$, $R^3$ and $R^4$ independently represent a hydrogen, a linear or branched alkyl group, or a linear or branched unsaturated alkyl group; $R^1$ and $R^2$, $R^2$ and $R^3$, and $R^3$ and $R^4$ may bind together to form an aromatic or aliphatic ring which may have one or more substituents of a linear or branched alkyl group, or a linear or branched unsaturated alkyl group; M represents a metal; m represents an integer of 3 or more; n represents an integer of 2 or more.

7 Claims, 4 Drawing Sheets

METAL COMPOUND OF AROMATIC HYDROXYCARBOXYLIC ACID, CHARGE CONTROL AGENT, TONER, AND POWDERY PAINT

This is a divisional application of Ser. No. 08/703,821 filed Aug. 27, 1996, now allowed, and the entire disclosure of this prior application is considered to be part of the disclosure of the accompanying application and is hereby incorporated by reference therein.

BACKGROUND OF THE INVENTION

1. Field of the Invention

The present invention relates to a metal compound of new structure having aromatic hydroxycarboxylic acid as ligand, a charge control agent or charge enhancer containing said compound as an active ingredient, and a toner for developing electrostatic images for electrophotography etc. or powdery paint for electrostatic painting containing said charge control agent or charge enhancer.

2. Description of the Prior Art

In copying machines, printers and other instruments based on electrophotography, various dry or wet toners containing a coloring agent, a fixing resin and other substances are used to develop the electrostatic latent image formed on the photoreceptor having a light-sensitive layer containing an inorganic or organic photoconductive substance.

Toner chargeability is a key factor in electrostatic latent image-developing systems. Thus, to appropriately control or stabilize the amount of toner charge, a charge control agent providing a positive or negative charge is often added to the toner.

Of the conventional charge control agents in actual application, those providing a positive charge for a toner include basic dyes such as nigrosine dyes and triarylmethane dyes, and electron donors such as quaternary ammonium salts. Charge control agents providing a negative charge for a toner include 2:1 type metal complexes of azo dyes.

However, most charge control agents of dye structure are usually structurally complex and lack stability; for example, they are likely to be decomposed or deteriorated to lose their expected charge control capability when they are exposed to mechanical friction or impact, temperature or humidity changes, electric impact, light irradiation, etc. Also, dyes lack versatility for use in color toners, because they are essentially chromatic.

Charge control agents free of these problems include chelate compounds having (alkyl)salicylic acid, hydroxynaphthoic acid, salicylaldehyde, phthalic acid, or the like, as ligand [e.g., 2:1 type Cr, Zn or Al complex of (alkyl)salicylic acid, 2:1 type boron complex of salicylic acid, 2:1 type Cr complex of hydroxynaphthoic acid, 2:1 type Cr or Co complex of salicylaldehyde, 2:1 type Cr or Fe complex of phthalic acid].

Although the charge control agents of complex structure mentioned here are mostly light in color and advantageously usable in color toners, some are unsatisfactory in terms of heat stability, dispersion uniformity in resin or charge control property, remaining to be further investigated.

Also, to improve paint adhesion efficiency in electrostatic painting with powdery paints, there have been attempts of applying charge control agents which have traditionally been used to control the charge of toners for developing electrostatic images.

Such attempts include an electrostatic powdery paint containing a resin polymer of an azine dye [Japanese Patent Unexamined Publication No. 67563/1985], a resin powder composition for electrostatic painting containing a charge enhancer like a metal-containing complex salt compound (Japanese Patent Unexamined Publication No. 75077/1988) and a powdery paint composition containing a quaternary ammonium salt as a charge control agent or charge enhancer (Japanese Patent Unexamined Publication No. 212563/1990).

However, these electrostatic powdery paints remain to be further improved in terms of environmental stability and heat resistance and durability under high-temperature conditions during powder painting.

The object of the present invention is to provide a metal compound of new chemical structure having an excellent charge control or charge-enhancing property; a charge control agent or charge enhancer which contains said metal compound as an active ingredient, which is excellent in environmental resistance (stability of charge control or charge-enhancing property to changes in temperature and humidity), storage stability (stability over time of charge control or charge-enhancing property), and especially heat stability and durability (charge control or charge-enhancing property stability in frequently repeated use), and which do not affect toner fixability or offset property when used in toners; and a toner for developing electrostatic images and powdery paint for electrostatic painting incorporating said charge control agent or charge enhancer.

SUMMARY OF THE INVENTION

The metal compound of the present invention, which has aromatic hydroxycarboxylic acid as ligand, is represented by formula [I] below.

wherein $R^1$, $R^2$, $R^3$ and $R^4$ independently represent a hydrogen, a linear or branched alkyl group, or a linear or branched unsaturated alkyl group; $R^1$ and $R^2$, $R^2$ and $R^3$, and $R^3$ and $R^4$ may bind together to form an aromatic or aliphatic ring which may have one or more substituents($R^x$) of a linear or branched alkyl group or a linear or branched unsaturated alkyl group; M represents a metal; m represents an integer of 3 or more; n represents an integer of 2 or more.

The metal compound of the present invention, which has aromatic hydroxycarboxylic acid as ligand, is preferably a 3:2 type (2 mol of center metal per 3 mol of ligand aromatic hydroxycarboxylic acid) metal compound represented by formula [II] below, or a 6:4 type (4 mol of center metal per 6 mol of ligand aromatic hydroxycarboxylic acid) metal compound represented by formula [III] below.

[II]

wherein R¹, R², R³ and R⁴ independently represent a hydrogen, a linear or branched alkyl group, or a linear or branched unsaturated alkyl group; R¹ and R², R² and R³, and R³ and R⁴ may bind together to form an aromatic or aliphatic ring which may have one or more substituents($R^x$) of a linear or branched alkyl group or a linear or branched unsaturated alkyl group; M represents a metal.

[III]

wherein R¹, R², R³ and R⁴ independently represent a hydrogen, a linear or branched alkyl group, or a linear or branched unsaturated alkyl group; R¹ and R², R² and R³, and R³ and R⁴ may bind together to form an aromatic or aliphatic ring which may have one or more substituents($R^x$) of a linear or branched alkyl group or a linear or branched unsaturated alkyl group; M represents a metal.

The metal compounds of the present invention, especially the 3:2 type and 6:4 type metal compounds, are stable in chemical structure and excellent in durability and heat resistance.

The charge control agent or charge enhancer of the present invention contains a metal compound represented by formula [I] above as an active ingredient.

The charge control agents or charge enhancers of the present invention, especially those having the 3:2 type metal compound and/or 6:4 type metal compound as an active ingredient, have good dispersibility in toner resin, are excellent in charge control or charge-enhancing property, environmental resistance, storage stability, and especially heat stability and durability, and do not affect toner fixability or offset property when used in a toner. Also, they cause almost no color deterioration in toner images even when added to various toners or electrostatic resin powders, because they are colorless or light in color.

The toner of the present invention for developing electrostatic images comprises the above-described charge control agent or charge enhancer of the present invention added for charge control, a coloring agent and a resin. It may contain one or more kinds of the metal compound represented by formula [I] above.

The toner of the present invention for developing electrostatic images is excellent in chargeability, environmental resistance, storage stability, and especially heat stability and durability, and have good fixability and offset property. Also, it causes almost no color deterioration in toner images, because the charge control agent or charge enhancer contained therein is colorless or light in color.

The powdery paint for electrostatic painting of the present invention comprises the above-described charge control agent or charge enhancer of the present invention and a resin. It may contain one or more kinds of the metal compound represented by formula [I] above.

The powdery paint for electrostatic painting of the present invention is excellent in charge control or charge-enhancing property, environmental resistance, storage stability, and especially heat stability and durability, showing stable charge control or charge-enhancing property even at high temperatures during electrostatic painting. Also, this powdery paint ensures almost 100% paint adhesion efficiency and is capable of forming a thick film of improved coating film performance and free of coating film defects. Furthermore, it causes almost no color deterioration in coating films, because the charge control agent or charge enhancer contained therein is colorless or light in color.

DETAILED DESCRIPTION OF THE INVENTION

Although m and n in formula [I] are normally an integer from 3 to 10 and an integer from 2 to 8, respectively, m and n may be 11 or more and 9 or more, respectively.

Although the center metal M for the metal compound of the present invention may be any metal, trivalent metals are preferred. Such metals include Cr, Al, Ti, Fe, Ni, Co, Mn, Si and Sn. Metals particularly preferable in terms of safety to the human body are Al, Ti and Fe.

The substituent for the aromatic hydroxycarboxylic acid as ligand of the metal compound of the present invention (substituent represented by R¹, R², R³ or R⁴, or $R^x$ above) is exemplified by linear or branched alkyl groups having about 1 to 12 carbon atoms, such as the methyl group, ethyl group, propyl group, isopropyl group, butyl group, isobutyl group, sec-butyl group, tert-butyl group, amyl group, isoamyl group, octyl group, tert-octyl group and dodecyl group, and unsaturated alkyl groups such as the allyl group, propenyl group and butenyl group, with greater preference given to the tert-butyl group and tert-octyl group.

The aromatic hydroxycarboxylic acid corresponding to the ligand of the metal compound of the present invention is exemplified by alkylsalicylic acids such as 4-tert-butylsalicylic acid,
3-methyl-salicylic acid,
3,5-di-tert-butylsalicylic acid,
4-isoamylsalicylic acid,
4-tert-octylsalicylic acid and
5-tert-octylsalicylic acid; and
alkyl-substitutional hydroxynaphthoic acids such as
3-hydroxy-7-methyl-2-naphthalenecarboxylic acid,
3-hydroxy-7-tert-butyl-2-naphthalenecarboxylic acid,
3-hydroxy-7-tert-octyl-2-naphthalenecarboxylic acid,
3-hydroxy-5,7-di-tert-butyl-2-naphthalenecarboxylic acid,
3-hydroxy-5,7-di-tert-octyl-2-naphthalenecarboxylic acid,
1-hydroxy-6-ethyl-2-naphthalenecarboxylic acid,
2-hydroxy-6-tert-butyl-1-naphthalenecarboxylic acid,
2-hydroxy-6-tert-octyl-1-naphthalenecarboxylic acid,
2-hydroxy-7-tert-butyl-1-naphthalenecarboxylic acid,
2-hydroxy-7-tert-octyl-1-naphthalenecarboxylic acid,
2-hydroxy-5,7-di-tert-butyl-1-naphthalenecarboxylic acid and
2-hydroxy-5,7-di-tert-octyl-1-naphthalenecarboxylic acid.

The metal compound of the present invention can be prepared by chelating the aromatic hydroxycarboxylic acid corresponding to the ligand in formula [I], [II] or [III] above with a metal provider (e.g., aluminum sulfate) by a known method, collecting the resulting product by filtration, and washing it.

Example metal providers which can be used to produce the metal compound of the present invention include aluminum compounds such as aluminum sulfate and basic aluminum acetate; chromium compounds such as chromium formate, chromium acetate, chromium sulfate, chromium chloride and chromium nitrate; iron compounds such as ferric chloride, ferric sulfate and ferric nitrate;

cobalt compounds such as cobalt chloride, cobalt nitrate and cobalt sulfate;

and titanium compounds such as titanium chloride.

Depending on reaction conditions (reaction pH and temperature, in particular) and differences in molar ratio of aromatic hydroxycarboxylic acid and metal provider in the charge mixture, the reaction product is obtained as a mixture containing in various content ratios the unreacted aromatic hydroxycarboxylic acid, a 2:1 type metal compound having aromatic hydroxycarboxylic acid as ligand, the 3:2 type metal compound of the present invention, and the metal compound of the present invention (especially a 6:4 type metal compound wherein x is 6 and y is 4) represented by the formula:

In this formula and the description below, represents an aromatic hydroxycarboxylic acid residue, and D represents the aromatic ring of the aromatic hydroxycarboxylic acid. In this formula, x represents an integer of 4 or more; y represents an integer of 3 or more.

The above-described 3:2 type and 6:4 type metal compounds of the present invention are both metal compounds wherein the molar ratio of ligand aromatic hydroxycarboxylic acid and center metal is 3:2. Although the molar ratio of aromatic hydroxycarboxylic acid and center metal in the raw material feed for production of these metal compounds is not subject to limitation, it is preferably 2:1 to 3:2. To obtain the above-described 3:2 type or 6:4 type metal compound at high yields, it is preferable that the reaction be carried out at a molar ratio of aromatic hydroxycarboxylic acid and center metal in the raw material feed of nearly 3:2 and a pH of 4 to 5.

Theoretically, the charges of the 3:2 type and 6:4 type metal compounds of the present invention are both zero. In the case of a mixture containing a known 2:1 type metal compound having an aromatic hydroxycarboxylic acid as ligand, in addition to a metal compound of the present invention, however, the mixture is partially or totally obtained as a proton acid. In such case, the reaction product can be derived as an acid, alkali metal salt, ammonium salt or organic ammonium salt.

The metal compound of the present invention is normally produced not as a single substance but as a mixture as described above, and is very difficult to separate even when various chromatographies are used. With this in mind, the metal compound of the present invention was identified by the FD-MS technique, known to preferentially reveal molecular ion peaks. Because the FD-MS technique is an soft ionization method, fragmentation is unlikely and a simple spectrum is obtained, resulting in the preferential demonstration of strong molecular ion peaks [Tsuchiya et al., "Current Progress of Mass Analysis" (in Japanese), Gendai Kagaku Extra Issue 15, 1988, Tokyo Kagaku Dojin; Mizuno, Kagaku to Kogyo, 64, 578, 507 (1990); Mizuno et al., Kagaku to Kogyo, 66, 569 (1992)]. This unique feature has been utilized to analyze insoluble organic dyes [Mizuno et al., Kagaku to Kogyo, 66, 569 (1992)] and to detect crown ether-diazonium salt complexes [K. Laali et al., J. Org. Chem., 54, 496 (1989)].

The molecular structure of the 3:2 type metal compound of the present invention is modeled by structures ①, ② and ③ below.

Chemical structures ① to ③ above, all deduced from molecular weight data obtained by FD-MS analysis, proved to be stable by chemical bond analysis based on the molecular orbital method.

The molecular structure of the 6:4 type metal compound of the present invention is modeled by structures ④ and ⑤ below.

-continued (5)

The above chemical structures, both deduced from molecular weight data obtained by FD-MS analysis, proved to be valid by chemical bond analysis based on the molecular orbital method.

It is possible to concentrate and purify a mixture containing in various content ratios the unreacted aromatic hydroxycarboxylic acid, and a 2:1 type metal compound, a 3:2 type metal compound, and a 6:4 type metal compound having aromatic hydroxycarboxylic acid as ligand to yield a 3:2 type or 6:4 type metal compound, on the basis of differences in solubility in organic solvents.

For example, concentration using an organic solvent is achieved as follows: Specifically, a 3:2 type or 6:4 type metal compound can be crystallized as the major component by dissolving a mixture containing in various content ratios the unreacted aromatic hydroxycarboxylic acid, and a 2:1 type metal compound, a 3:2 type metal compound, and a 6:4 type metal compound having aromatic hydroxycarboxylic acid as ligand in an organic solvent of high dissolving capacity (e.g., chloroform), and adding drop by drop another organic lo solvent of low dissolving capacity for the 3:2 type or 6:4 type metal compounds (e.g., methanol).

Examples of the 3:2 type metal compound (left Example Compound column) and 6:4 type metal compound (right Example Compound column) of the present invention are given in Table 1 but are not limitative to the present invention.

TABLE 1

| Example Compound | | Aromatic hydroxycarboxylic acid residue | Center metal |
|---|---|---|---|
| $[Dr]_3 (M)_2$ | $[Dr]_6 (M)_4$ | Dr | M |
| Example Compound 1 | Example Compound 2 | t-$C_4H_9$, t-$C_4H_9$, COO (phenyl) | Al |
| Example Compound 3 | Example Compound 4 | $CH_3$, COO (phenyl) | Al |
| Example Compound 5 | Example Compound 6 | t-$C_4H_9$, t-$C_8H_{17}$, COO (phenyl) | Al |
| Example Compound 7 | Example Compound 8 | t-$C_8H_{17}$, COO (phenyl) | Al |
| Example Compound 9 | Example Compound 10 | t-$C_4H_9$, COO (naphthyl) | Al |

TABLE 1-continued

| Example Compound | | Aromatic hydroxycarboxylic acid residue | Center metal |
|---|---|---|---|
| [Dr]₃ (M)₂ | [Dr]₆ (M)₄ | Dr | M |
| Example Compound 11 | Example Compound 12 | 3,6-di-t-C₄H₉-substituted naphthalene with O and COO groups | Al |
| Example Compound 13 | Example Compound 14 | 6-t-C₄H₉-substituted naphthalene with O and COO groups | Al |
| Example Compound 15 | Example Compound 16 | iso-C₅H₁₁-substituted benzene with O and COO groups | Cr |
| Example Compound 17 | Example Compound 18 | 3,5-di-t-C₄H₉-substituted benzene with O and COO groups | Cr |
| Example Compound 19 | Example Compound 20 | t-C₄H₉-substituted benzene with O and COO groups | Cr |
| Example Compound 21 | Example Compound 22 | 6-t-C₄H₉-substituted naphthalene with O and COO groups | Cr |
| Example Compound 23 | Example Compound 24 | 3,5-di-t-C₄H₉-substituted benzene with O and COO groups | Ti |
| Example Compound 25 | Example Compound 26 | iso-C₃H₇, t-C₄H₉-substituted benzene with O and COO groups | Ti |

TABLE 1-continued

| Example Compound | | Aromatic hydroxycarboxylic acid residue | Center metal |
|---|---|---|---|
| [Dr]₃ (M)₂ | [Dr]₆ (M)₄ | Dr | M |
| Example Compound 27 | Example Compound 28 |  | Ti |
| Example Compound 29 | Example Compound 30 |  | Ti |
| Example Compound 31 | Example Compound 32 |  | Co |
| Example Compound 33 | Example Compound 34 |  | Co |
| Example Compound 35 | Example Compound 36 |  | Fe |
| Example Compound 37 | Example Compound 38 |  | Fe |
| Example Compound 39 | Example Compound 40 |  | Fe |
| Example Compound 41 | Example Compound 42 |  | Fe |

TABLE 1-continued

| Example Compound | | Aromatic hydroxycarboxylic acid residue | Center metal |
|---|---|---|---|
| [Dr]$_3$ (M)$_2$ | [Dr]$_6$ (M)$_4$ | Dr | M |
| Example Compound 43 | Example Compound 44 | t-C$_4$H$_9$, t-C$_4$H$_9$ substituted naphthalene with O and COO | Fe |
| Example Compound 45 | Example Compound 46 | t-C$_8$H$_{17}$ substituted naphthalene with O and COO | Fe |
| Example Compound 47 | Example Compound 48 | t-C$_4$H$_9$ substituted naphthalene with O and COO | Fe |
| Example Compound 49 | Example Compound 50 | t-C$_4$H$_9$, t-C$_4$H$_9$ substituted benzene with O and COO | Mn |

The charge control agent or charge enhancer of the present invention contains a metal compound represented by formula [I] above as an active ingredient.

The charge control agent or charge enhancer of the present invention is excellent in charge control or charge-enhancing property, environmental resistance, storage stability, and especially heat stability and durability, and does not affect toner fixability or offset property when used in toners.

The charge control agent or charge enhancer of the present invention is preferably a 3:2 type metal compound represented by formula [II] above or a 6:4 type metal compound represented by formula [III] above.

Although the center metal M for the metal compound of formula [I], [II] and [III] may be any metal, trivalent metals are preferred. Such metals include Cr, Al, Ti, Fe, Ni, Co, Mn, Si and Sn. Metals particularly preferable in terms of safety to the human body are Al, Ti and Fe.

The charge control agent or charge enhancer of the present invention may also contain a 2:1 type metal compound represented by formula [IV] below, which has aromatic hydroxycarboxylic acid as ligand and possesses charge control or charge-enhancing property.

[IV]

wherein $R^1$, $R^2$, $R^3$ and $R^4$ independently represent a hydrogen, a linear or branched alkyl group, or a linear or branched unsaturated alkyl group; $R^1$ and $R^2$, $R^2$ and $R^3$, and $R^3$ and $R^4$ may bind together to form an aromatic or aliphatic ring which may have one or more substituents($R^x$) of a linear or branched alkyl group or a linear or branched unsaturated alkyl group; M represents the same metal as that in formula [I]; $A^+$ represents a cation such as $H^+$, an alkali metal cation, $NH_4^+$ or an organic ammonium.

The charge control agent or charge enhancer of the present invention may also contain a metal salt of aromatic hydroxycarboxylic acid possessing a charge control or charge-enhancing property, which metal salt is represented by formula [V] below.

wherein $R^1$, $R^2$, $R^3$ and $R^4$ independently represent a hydrogen, a linear or branched alkyl group, or a linear or branched unsaturated alkyl group; $R^1$ and $R^2$, $R^2$ and $R^3$, and $R^3$ and $R^4$ may bind together to form an aromatic or aliphatic ring which may have one or more substituents($R^x$) of a linear or branched alkyl group or a linear or branched unsaturated alkyl group; M represents the same metal as that in formula [I]; p and q each represent a positive integer, (p+q) representing the oxidation number of metal M.

Examples of $R^1$, $R^2$, $R^3$ and $R^4$, and $R^x$ for formula [IV] and [V] are the same as those for formula [I].

The charge control agent or charge enhancer of the present invention may also contain a small amount of aromatic hydroxycarboxylic acid as an unreacted starting material, and other substances.

The toner of the present invention for developing electrostatic images comprises the above-described charge control agent or charge enhancer of the present invention added for charge control, a coloring agent and a resin. It may contain one or more kinds of the metal compound represented by formula [I], [II] or [III] above.

The toner of the present invention for developing electrostatic images is excellent in environmental resistance, storage stability, and especially heat stability and durability, and have good fixability and offset property.

The toner of the present invention for developing electrostatic images can serve the purpose, as long as it contains the charge control agent or charge enhancer of the present invention in an amount enabling charge control. Preferably, the content ratio of charge control agent or charge enhancer is 0.1 to 10 parts by weight of the metal compound represented by formula [I], [II] or [III], or 0.1 to 10 parts by weight of the combination of the metal compound represented by formula [I], [II] or [III] and the metal compound represented by formula [IV], per 100 parts by weight of resin, more preferably 0.5 to 5 parts by weight per 100 parts by weight of resin.

Example resins useful in the toner of the present invention include the following known resins or binder resins for use in toners. Specifically, styrene resin, styrene-acrylic resin, styrene-butadiene resin, styrene-maleic acid resin, styrene-vinyl methyl ether resin, styrene-methacrylic acid ester copolymer, phenol resin, epoxy resin, polyester resin, polypropylene resin, paraffin wax, etc. These resins may be used singly or in blends.

The toner of the present invention may incorporate various dyes and pigments as coloring agents. Examples of useful coloring agents include organic pigments such as Quinophthalone Yellow, Isoindolinone Yellow, Perinone Orange, Perylene Maroon, Rhodamine 6G Lake, Quinacridone Red, Rose Bengale, copper Phthalocyanine Blue, copper Phthalocyanine Green and diketopyrrolopyrrole pigments; and inorganic pigments such as Carbon Black, Titanium White, Titanium Yellow, Ultramarine, Cobalt Blue and Red Iron Oxide.

Examples of useful coloring agents for use in color toners include various oil-soluble or dispersion dyes such as azo dyes, quinophthalone dyes, anthraquinone dyes, phthalocyanine dyes, indophenol dyes and indoaniline dyes; and triarylmethane dyes and xanthene dyes modified with resins such as rosin, rosin-modified phenol and rosin-modified maleic acid.

The toner of the present invention for developing electrostatic images may incorporate the above-mentioned coloring agents singly or in combination. Chromatic monocolor toners may incorporate an appropriate combination of a dye and pigment of the same color tone, e.g., a quinophthalone dye and pigment, a xanthene or rhodamine dye and pigment, or a phthalocyanine dye and pigment.

To improve toner quality, additives such as electroconductive grains, fluidity-improving agents and image peeling-preventing agents may be added internally or externally.

The toner of the present invention for developing electrostatic images can, for example, be produced as follows: After a resin and coloring agent as described above, the charge control agent of the present invention, and, if necessary, a magnetic material, a fluidizing agent and other additives, are thoroughly mixed using a ball mill or another mechanical mixer, the mixture is kneaded in a molten state using a hot kneader such as a heat roll, kneader or extruder. The resulting molten mixture is cooled and solidified, followed by pulverization and particle classification by size, to yield a toner 5 to 20 μm in mean particle diameter.

Other usable methods include the method in which other starting materials are dispersed in a binder resin solution and then spray dried to yield a toner, and the method in which a given set of starting materials are mixed in a monomer for binder resin to yield an emulsified suspension, which is then polymerized to yield a polymeric toner.

When the toner of the present invention for developing electrostatic images is used as a two-component developer, development can be achieved by the two-component magnetic brush developing process or the like using the toner in mixture with carrier powder.

Any known carrier can be used. Examples of the carrier include iron powder, nickel powder, ferrite powder and glass beads about 50 to 200 μm in particle diameter, and such materials as coated with acrylic acid ester copolymer, styrene-acrylic acid ester copolymer, styrene-methacrylic acid ester copolymer, silicone resin, polyamide resin, ethylene fluoride resin or the like.

When the toner of the present invention for developing electrostatic images is used as a one-component developer, an appropriate amount of fine powder of a ferromagnetic material such as iron powder, nickel powder or ferrite powder may be added and dispersed in preparing the toner as described above. Examples of developing processes which can be used in this case include contact development and jumping development.

The powdery paint for electrostatic painting of the present invention comprises the above-described charge control agent or charge enhancer of the present invention and a resin. It may contain one or more kinds of the metal compound represented by formula [I], [II] or [III] above.

The powdery paint for electrostatic painting of the present invention is excellent in environmental resistance, storage stability, and especially heat stability and durability; it ensures almost 100% paint adhesion efficiency and is capable of forming a thick film of improved coating film performance and free of coating film defects.

The powdery paint for electrostatic painting of the present invention can serve the purpose, as long as it contains the charge control agent or charge enhancer of the present invention in an amount enabling charge control or enhancement. Preferably, the content ratio of charge control agent or charge enhancer is 0.1 to 10 parts by weight of the metal compound represented by formula [I], [II] or [III], or 0.1 to 10 parts by weight of the combination of the metal compound represented by formula [I], [II] or [III] and the metal compound represented by formula [IV], per 100 parts by weight of resin, more preferably 0.5 to 5 parts by weight per 100 parts by weight of resin.

Example resins useful in the powdery paint for electrostatic painting of the present invention include thermoplastic resins such as styrene resin, styrene-acrylic resin, styrene-butadiene resin, styrene-maleic acid resin, styrene-vinyl methyl ether resin, styrene-methacrylic acid ester copolymer, polyester resin and polypropylene resin; and thermosetting resins such as phenol resin and epoxy resin. These resins may be used singly or in blends.

The powdery paint for electrostatic painting of the present invention may incorporate dyes, pigments, metal powders, etc. as coloring agents, fluidity-improving agents, filling agents, hardening agents, plasticizers, etc., according to the use and purpose thereof.

Example coloring agents which can be used in the powdery paint for electrostatic painting of the present invention include organic pigments such as Quinophthalone Yellow, Isoindolinone Yellow, Perinone Orange, Perylene Maroon, Rhodamine 6G Lake, Quinacridone Red, Rose Bengale, copper Phthalocyanine Blue, copper Phthalocyanine Green and diketopyrrolopyrrole pigments; inorganic pigments such as Carbon Black, Titanium White, Titanium Yellow, Ultramarine, Cobalt Blue, Red Iron Oxide and aluminum powder; and metal powders.

The powdery paint for electrostatic painting of the present invention can, for example, be produced as follows: A charge control agent or charge enhancer and resin as described above, and, if necessary, a coloring agent, fluidity-improving agent, filling agent, hardening agent, plasticizer and other additives chosen according to the use and purpose thereof, are thoroughly mixed using a ball mill or another mechanical mixer. The mixture is kneaded in a molten state using a hot kneader such as a heat roll, kneader or extruder, after which it is cooled and solidified, followed by pulverization and particle classification by size, to yield a powdery paint for electrostatic painting having a desired particle diameter of 10 to 250 $\mu$m.

Other usable methods include the method in which other starting materials are dispersed in a resin solution and then spray dried to yield a powdery paint, and the method in which a given set of starting materials are mixed in a monomer for resin to yield an emulsified suspension, which is then polymerized to yield a powdery paint.

Painting with the powdery paint for electrostatic painting of the present invention can be achieved using an ordinary method of electrostatic powder painting such as the corona charging method, frictional charging method or hybrid method.

EXAMPLES

The present invention is hereinafter described in more detail by means of the following examples, which are not to be construed as limitative on the present invention.

Example syntheses of metal compounds of the present invention are described in Examples 1 through 13.

Example 1

(Synthesis of Example Product 1)

30 g (0.12 mol) of 3,5-di-tert-butylsalicylic acid and 7.2 g (0.18 mol) of sodium hydroxide were added to 300 ml of water and dissolved under heating at 60° C. Separately, 10.3 g (0.03 mol) of aluminum sulfate was added to 300 ml of water and dissolved under heating at 60° C. To the latter solution, the former solution, i.e., a solution of 3,5-di-tert-butylsalicylic acid, was added drop by drop over a period of 20 minutes.

After completion of the addition, the mixture was heated to 90° C. and reacted for 1 hour during stirring, after which the precipitate was collected by filtration, washed with water, and dried at 100 to 120° C., to yield 28.5 g of a white powder (Example Product 1) containing Example Compound 1.

This powder was pulverized using a desktop pulverizer to yield a powder having a bulk density of 8.3 cc/g. An experimental toner was prepared and the amount of charges of this powder was determined to be −55.1 $\mu$C/g using a powder blowoff charge analyzer [MODEL TB200 (trade name), produced by Toshiba Chemical Corporation).

Figure 1:
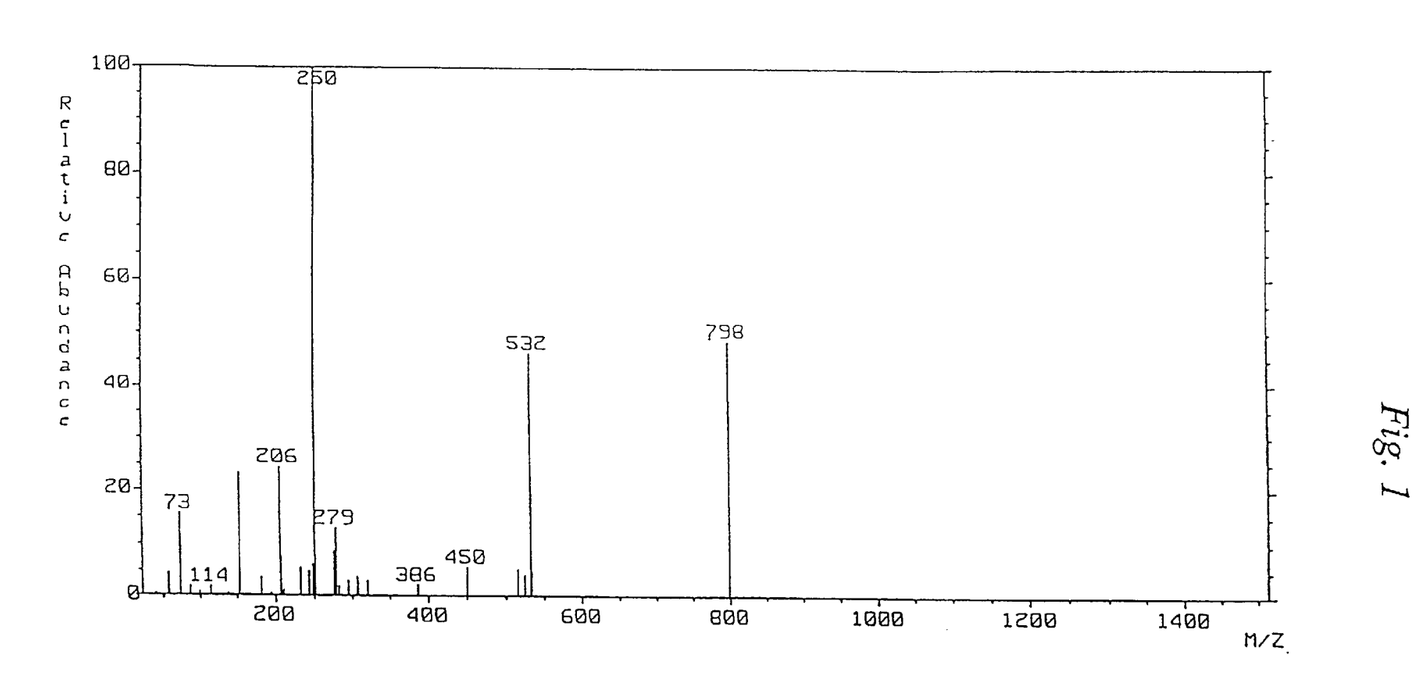
FIG. 1 is a mass spectrum of Example Product 1 taken by the FD-MS technique.
Figure 2:
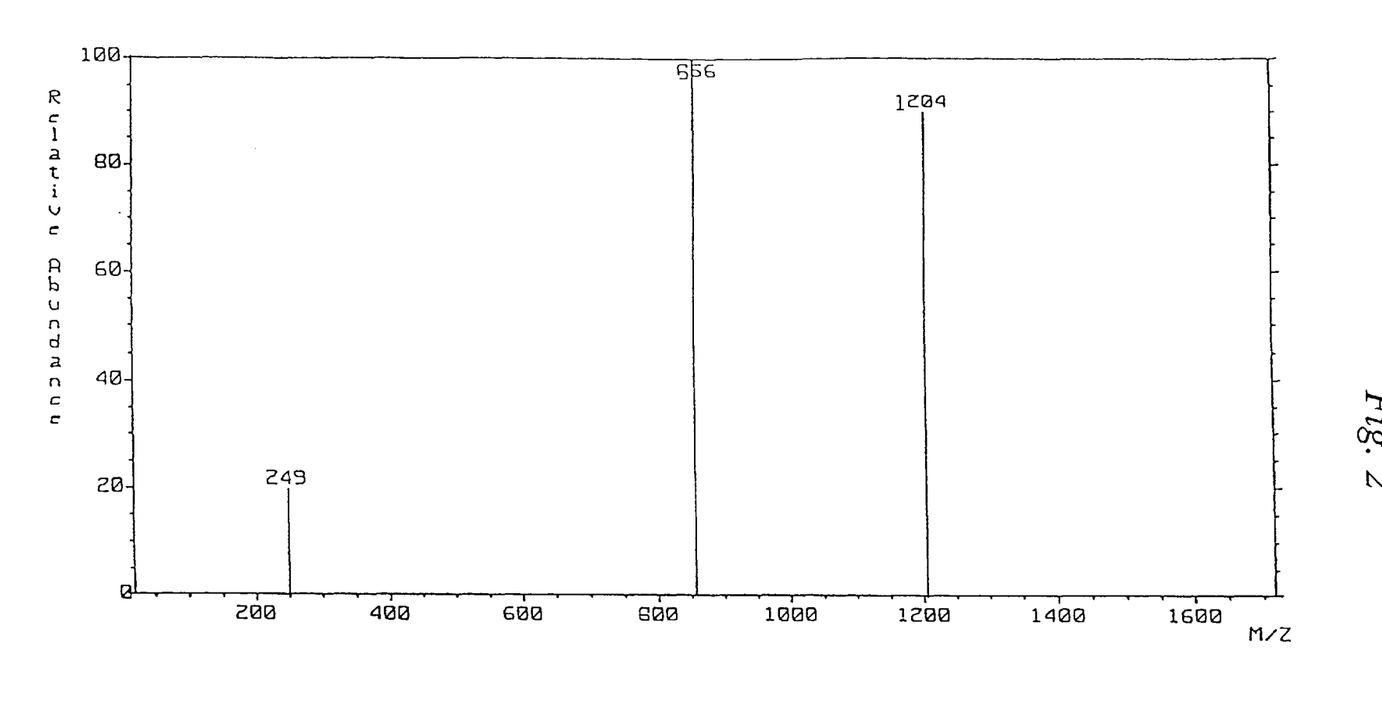
FIG. 2 is a mass spectrum of Example Product 3 taken by the FD-MS technique.
Figure 3:
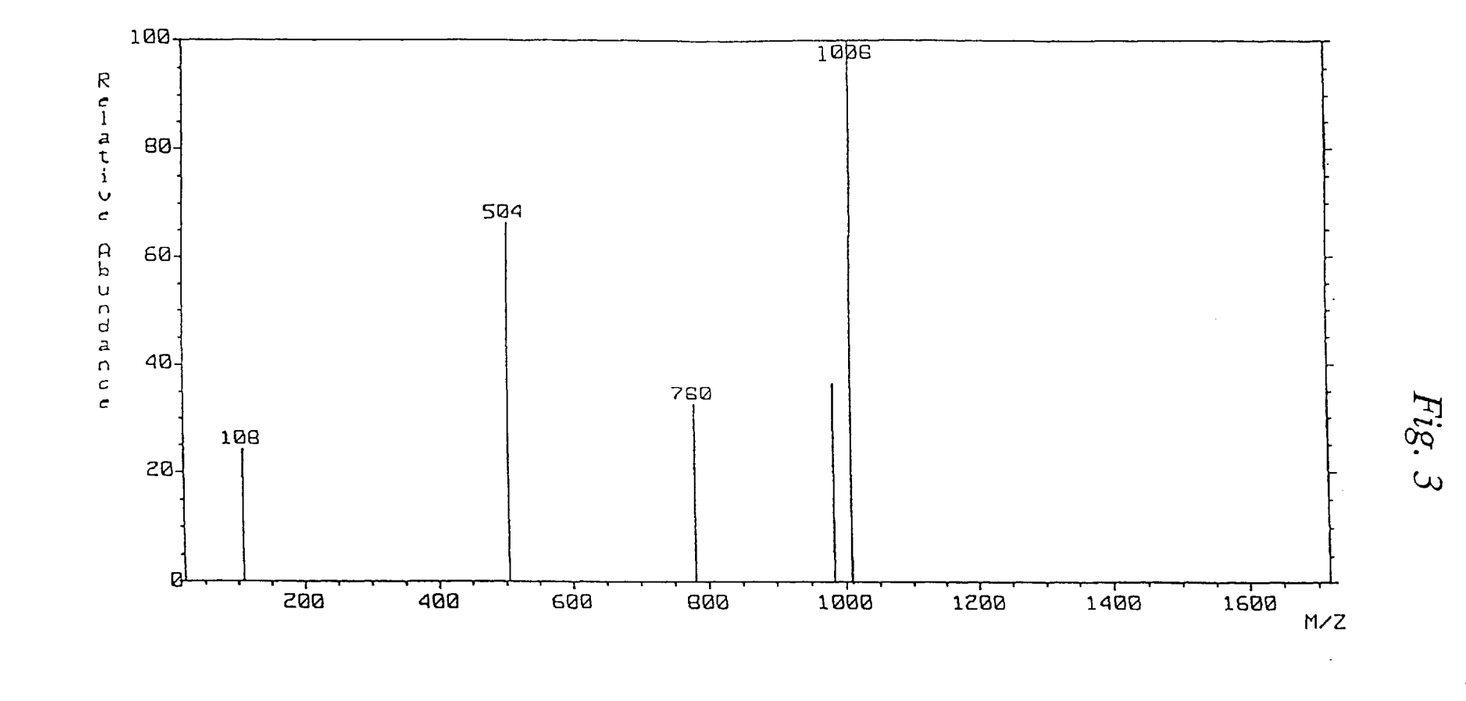
FIG. 3 is a mass spectrum of Example Product 6 taken by the FD-MS technique.
Figure 4:
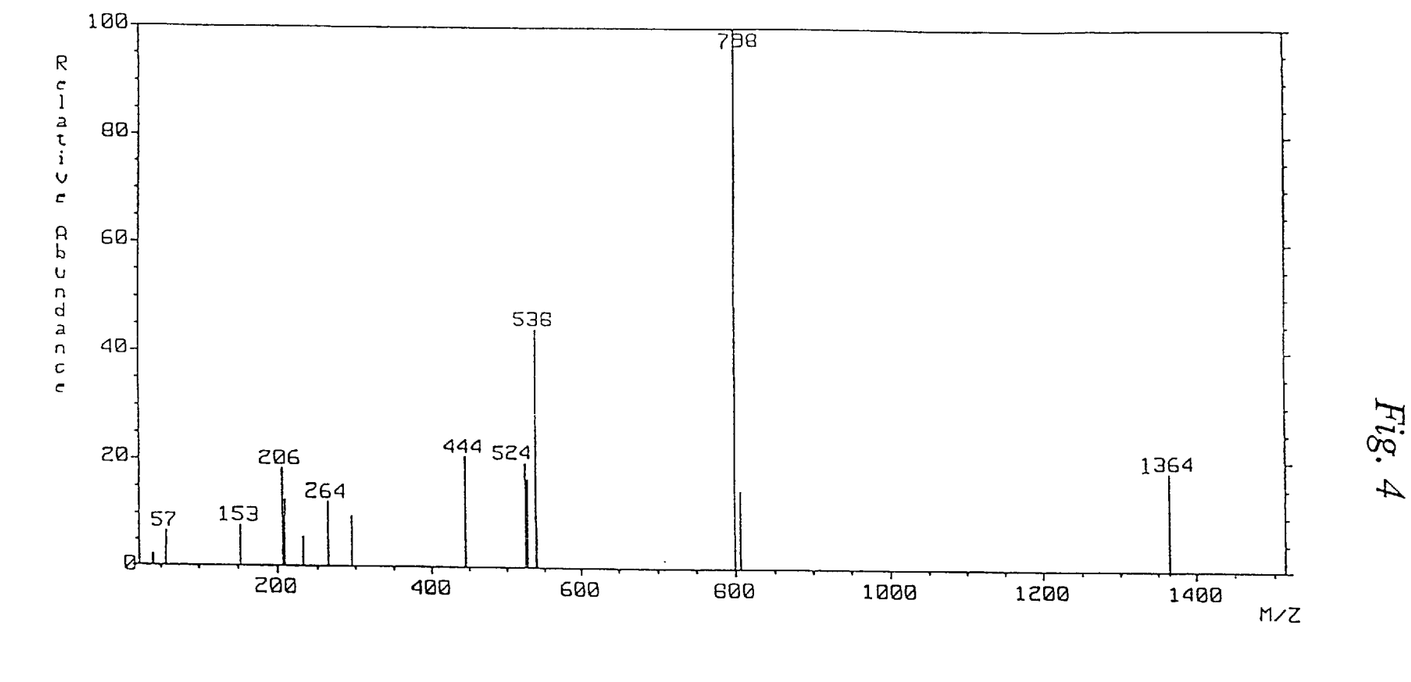
FIG. 4 is a mass spectrum of Example Product 12 taken by the FD-MS technique.

A powder of Example Product 1 was subjected to molecular weight determination by the FD-MS technique under analytical conditions A; the mass spectrum shown in FIG. 1 was obtained [the abscissa indicates M/Z (mass/charge) and the ordinate indicates relative abundance (content ratio); the same applies to FIGS. 2 through 4]. The mass spectrum of FIG. 1 demonstrated 3 peaks for 3:2 type metal compound of Example Compound 1 (molecular weight M/Z, 798 [M$^+$]), unreacted 3,5-di-tert-butylsalicylic acid (molecular weight M/Z, 250 [M$^+$]) and 2:1 type metal compound (molecular weight M/Z, 532 [M$^+$]).

*Molecular weight determination by the FD-MS technique

The sample, dissolved or dispersed in DMF, was analyzed using a mass analyzer [JMS-DX303HF (trade name), produced by JEOL Ltd.] to obtain a mass spectrum showing the sample's molecular weight.

Analytical conditions A: FD-MS (Field Desorption Mass Spectroscopy) technique (field leaving ionization method)
  Carbon emitter used
  Resolution: 500, 35–1700 M/z
  Acceleration voltage: 2.5 kV
  Ion multiplier: 1.7–2.5 kV
  Emitter amperage: 0–40 mA
  Cathode voltage: 5.0 kV Analytical conditions B: FD-MS technique (field leaving ionization method)
  Carbon emitter used
  Resolution: 1500, 35–1700 M/Z
  Acceleration voltage: 2.5 kV
  Ion multiplier: 1.8–2.2 kV
  Emitter amperage: 0–40 mA
  Cathode voltage: 5.0 kV Example 2

(Synthesis of Example Product 2)

30 g (0.12 mol) of 3,5-di-tert-butylsalicylic acid and 6.0 g (0.15 mol) of sodium hydroxide were added to 300 ml of water and dissolved under heating at 60° C. Separately, 11.8 g (0.3 mol) of chromic sulfate and 9.0 g (0.07 mol) of sodium acetate trihydrate were added to 300 ml of water and dissolved under heating at 60° C. To the latter solution, the former solution, i.e., a solution of 3,5-di-tert-butylsalicylic acid, was added drop by drop over a period of 20 minutes.

After completion of the addition, the mixture was heated to 90° C. and reacted for 2 hours during stirring, after which the precipitate was collected by filtration, washed with water, and dried at 100 to 120° C., to yield 27.2 g of a light-green powder (Example Product 2) containing Example Compounds 17 and 18.

This powder was pulverized using a desktop pulverizer to yield a powder having a bulk density of 4.5 cc/g. An experimental toner was prepared and the amount of charges of this powder was determined to be $-69.0$ $\mu$C/g in the same manner as in Example 1.

Example 3

(Synthesis of Example Product 3)

30 g (0.12 mol) of 3,5-di-tert-butylsalicylic acid and 7.2 g (0.18 mol) of sodium hydroxide were added to 300 ml of water and dissolved under heating at 60° C . Separately, 9.7 g (0.06 mol) of ferric chloride was added to 300 ml of water and dissolved under heating at 60° C. To the latter solution, the former solution of 3,5-di-tert-butylsalicylic acid was added drop by drop over a period of 20 minutes.

After completion of the addition, the mixture was heated to 90° C. and reacted for 2 hours during stirring, after which the precipitate was collected by filtration, washed with water, and dried at 100 to 120° C., to yield 29.7 g of a light-black powder (Example Product 3) containing Example Compound 35.

This powder was pulverized using a desktop pulverizer to yield a powder having a bulk density of 7.5 cc/g. An experimental toner was prepared and the amount of charges of this powder was determined to be $-41.3$ $\mu$C/g in the same manner as in Example 1.

A powder of Example Product 3 was subjected to molecular weight determination by the FD-MS technique under analytical conditions B; the mass spectrum shown in FIG. 2 was obtained. The mass spectrum of FIG. 2 demonstrated 3 peaks for a 3:2 type metal compound of Example Compound 35 (molecular weight M/Z, 856 [M$^+$]), unreacted 3,5-di-tert-butylsalicylic acid (molecular weight M/Z, 249 [(M$-$1)$^+$]) and an m:n type metal compound wherein m represents an integer of 4 or more and n represents an integer of 3 or more (molecular weight M/Z, 1204 [M$^+$]).

Example 4

(Synthesis of Example Product 4)

30 g (0.12 mol) of 3,5-di-tert-butylsalicylic acid and 7.2 g (0.18 mol) of sodium hydroxide were added to 300 ml of water and dissolved under heating at 60° C. Separately, 9.3 g (0.06 mol) of titanium trichloride was added to 300 ml of water and dissolved under heating at 60° C. To the latter solution, the former solution of 3,5-di-tert-butylsalicylic acid was added drop by drop over a period of 20 minutes.

After completion of the addition, the mixture was heated to 90° C. and reacted for 2 hours during stirring, after which the precipitate was collected by filtration, washed with water, and dried at 100 to 120° C., to yield 25.2 g of a light-black powder (Example Product 4) containing Example Compounds 25 and 26.

This powder was pulverized using a desktop pulverizer to yield a powder having a bulk density of 6.4 cc/g. An experimental toner was prepared and the amount of charges of this powder was determined to be $-41.2$ $\mu$C/g in the same manner as in Example 1.

Example 5

(Synthesis of Product 5)

30 g (0.12 mol) of 5-tert-octylsalicylic acid and 7.2 g (0.18 mol) of sodium hydroxide were added to 300 ml of water and dissolved under heating at 60° C. Separately, 10.3 g (0.03 mol) of aluminum sulfate was added to 300 ml of water and dissolved under heating at 60° C. To the latter solution, the former solution of 5-tert-octylsalicylic acid was added drop by drop over a period of 20 minutes.

After completion of the addition, the mixture was heated to 90° C. and reacted for 1 hour during stirring, after which the precipitate was collected by filtration, washed with water, and dried at 100 to 120° C., to yield 31.6 g of a white powder (Example Product 5) containing Example Compound 7.

This powder was pulverized using a desktop pulverizer to yield a powder having a bulk density of 8.4 cc/g. An experimental toner was prepared and the amount of charges of this powder was determined to be $-58.4$ $\mu$C/g in the same manner as in Example 1.

Example 6

(Synthesis of Example Product 6)

18 g (0.12 mol) of 3-methylsalicylic acid and 7.2 g (0.18 mol) of sodium hydroxide were added to 300 ml of water and dissolved under heating at 60° C. Separately, 10.3 g (0.03 mol) of aluminum sulfate was added to 300 ml of water and dissolved under heating at 60° C. To the latter solution, the former solution of 3-methylsalicylic acid was added drop by drop over a period of 20 minutes.

After completion of the addition, the mixture was heated to 90° C. and reacted for 1 hour during stirring, after which the precipitate was collected by filtration, washed with water, and dried at 100 to 120° C., to yield 14.0 g of a white powder (Example Product 6) containing Example Compounds 3 and 4.

This powder was pulverized using a desktop pulverizer to yield a powder having a bulk density of 7.1 cc/g. An experimental toner was prepared and the amount of charges of this powder was determined to be $-44.5$ $\mu$C/g in the same manner as in Example 1.

This powder was subjected to molecular weight determination by the FD-MS technique under analytical conditions B; the mass spectrum shown in FIG. 3 was obtained. The mass spectrum of FIG. 3 demonstrated the presence of a 3:2 type metal compound of Example Compound 3 (molecular weight M/Z, 504 [M$^+$]) and a 6:4 type metal compound of Example Compound 4 (molecular weight M/Z, 1008 [M$^+$]).

Example 7

(Synthesis of Example Product 7)

30 g (0.12 mol) of 3,5-di-tert-butylsalicylic acid and 7.2 g (0.18 mol) of sodium hydroxide were added to 300 ml of water and dissolved under heating at 60° C. Separately, 13.4 g (0.04 mol) of aluminum sulfate was added to 300 ml of water and dissolved under heating at 60° C. To the latter solution, the former solution of 3,5-di-tert-butylsalicylic acid was added drop by drop over a period of 20 minutes.

After completion of the addition, the mixture was heated to 90° C. and reacted for 1 hour during stirring, after which the precipitate was collected by filtration, washed with water, and dried at 100 to 120° C., to yield 27.2 g of a white powder (Example Product 7) containing Example Compound 1.

This powder was pulverized using a desktop pulverizer to yield a powder having a bulk density of 7.9 cc/g. An experimental toner was prepared and the amount of charges of this powder was determined to be $-60.1$ $\mu$C/g in the same manner as in Example 1.

Example 8

(Synthesis of Example Product 8)

30 g (0.12 mol) of 3,5-di-tert-butylsalicylic acid and 6.0 g (0.15 mol) of sodium hydroxide were added to 300 ml of water and dissolved under heating at 60° C. Separately, 15.7 g (0.4 mol) of chromic sulfate and 9.0 g (0.07 mol) of sodium acetate trihydrate were added to 300 ml of water and dissolved under heating at 60° C. To the latter solution, the former solution, i.e., a solution of 3,5-di-tert-butylsalicylic acid, was added drop by drop over a period of 20 minutes.

After completion of the addition, the mixture was heated to 90° C. and reacted for 2 hours during stirring, after which the precipitate was collected by filtration, washed with water, and dried at 100 to 120° C., to yield 28.5 g of a light-green powder (Example Product 8) containing Example Compounds 17 and 18.

This powder was pulverized using a desktop pulverizer to yield a powder having a bulk density of 4.7 cc/g. An experimental toner was prepared and the amount of charges of this powder was determined to be $-70.0$ $\mu$C/g in the same manner as in Example 1.

Example 9

(Synthesis of Example Product 9)

29.3 g (0.12 mol) of 3-hydroxy-7-tert-butyl-2-naphthalenecarboxylic acid and 7.2 g (0.18 mol) of sodium hydroxide were added to 300 ml of water and dissolved under heating at 60° C. Separately, 10.3 g (0.03 mol) of aluminum sulfate was added to 300 ml of water and dissolved under heating at 60° C. To the latter solution, the former solution of 3-hydroxy-7-tert-butyl-2-naphthalenecarboxylic acid was added drop by drop over a period of 20 minutes.

After completion of the addition, the mixture was heated to 90° C. and reacted for 1 hour during stirring, after which the precipitate was collected by filtration, washed with water, and dried at 100 to 120° C., to yield 29.0 g of a light-yellow powder (Example Product 9) containing Example Compounds 9 and 10.

This powder was pulverized using a desktop pulverizer to yield a powder having a bulk density of 8.2 cc/g. An experimental toner was prepared and the amount of charges of this powder was determined to be $-45.3$ $\mu$C/g in the same manner as in Example 1.

Example 10

(Synthesis of Example Product 10)

29.3 g (0.12 mol) of 2-hydroxy-7-tert-butyl-1-naphthalenecarboxylic acid and 7.2 g (0.18 mol) of sodium hydroxide were added to 300 ml of water and dissolved under heating at 60° C. Separately, 10.3 g (0.03 mol) of aluminum sulfate was added to 300 ml of water and dissolved under heating at 60° C. To the latter solution, the former solution of 2-hydroxy-7-tert-butyl-1-naphthalenecarboxylic acid was added drop by drop over a period of 20 minutes.

After completion of the addition, the mixture was heated to 90° C. and reacted for 1 hour during stirring, after which the precipitate was collected by filtration, washed with water, and dried at 100 to 120° C., to yield 29.2 g of a white powder (Example Product 10) containing Example Compounds 13 and 14.

This powder was pulverized using a desktop pulverizer to yield a powder having a bulk density of 8.1 cc/g. An experimental toner was prepared and the amount of charges of this powder was determined to be $-45.7$ $\mu$C/g in the same manner as in Example 1.

Example 11

(Synthesis of Example Product 11)

36 g (0.12 mol) of 3-hydroxy-7-tert-octyl-2-naphthalenecarboxylic acid and 7.2 g (0.18 mol) of sodium hydroxide were added to 300 ml of water and dissolved under heating at 60° C. Separately, 9.3 g (0.3 mol) of titanium trichloride was added to 300 ml of water and dissolved under heating at 60° C. To the latter solution, the former solution of 3-hydroxy-7-tert-octyl-2-naphthalenecarboxylic acid was added drop by drop over a period of 20 minutes.

After completion of the addition, the mixture was heated to 90° C. and reacted for 2 hours during stirring, after which the precipitate was collected by filtration, washed with water, and dried at 100 to 120° C., to yield 35.3 g of a reddish light-yellow powder (Example Product 11) containing Example Compounds 29 and 30.

This powder was pulverized using a desktop pulverizer to yield a powder having a bulk density of 7.9 cc/g. An experimental toner was prepared and the amount of charges of this powder was determined to be $-45.5$ $\mu$C/g in the same manner as in Example 1.

Examples 12 and 13 show examples in which a metal compound of the present invention was concentrated by subjecting the white powder (Example Product 1) of Example 1 to solvent purification.

Example 12

(Production of Example Product 12)

50 g of the white powder obtained in Example 1 was dissolved in 100 ml of chloroform. To this solution, 300 ml of methanol was added drop by drop to separate a crystal, which was then collected by filtration. This procedure was repeated in 3 cycles; the resulting crystal was dried to yield 7.1 g of a white powder (Example Product 12).

This powder was subjected to molecular weight determination by the FD-MS technique under analytical conditions B; the mass spectrum shown in FIG. 4 was obtained. The mass spectrum of FIG. 4 demonstrated that the peak for unreacted 3,5-di-tert-butylsalicylic acid (molecular weight M/Z, 250 [M$^+$]) disappeared, and that a 3:2 type metal compound of Example Compound 1 (molecular weight M/Z, 798 (M$^+$]) was concentrated.

Example 13

(Production of Example Product 13)

50 g of the white powder obtained in Example 1 was dissolved in 100 ml of chloroform. To this solution, 500 ml of acetonitrile was added drop by drop to separate a crystal, which was then collected by filtration. This procedure was repeated in 3 cycles; the resulting crystal was dried to yield 5.8 g of a white powder (Example Product 13).

The Al content in Example Product 12 was determined by the atomic absorption method using an atomic absorption analyzer [AA-660 (trade name), produced by Shimadzu Corporation]; the Al content was found to be 6.52% by weight. Separately, the water content in Example Product 11 was determined by Karl Fisher's method using a Karl Fisher moisture meter [MKA-210 (trade name), produced by Kyoto Denshi]; the water content was found to be 4.3% by weight.

These analytical results agree well with the data on a 3:2 type metal compound bound with 2 water molecules (theoretical Al content=6.5% by weight).

Table 2 shows the identities and molecular weights of the metal compounds obtained in Examples 1 through 13.

TABLE 2

| Example No. | D⟨COOH, OH⟩ | Molecular weight | M | Atomic number |
|---|---|---|---|---|
| Example 1 | 3,5-di-tert-butylsalicylic acid | 250 | Al | 27 |
| Example 2 | 3,5-di-tert-butylsalicylic acid | 250 | Cr | 52 |
| Example 3 | 3,5-di-tert-butylsalicylic acid | 250 | Fe | 56 |
| Example 4 | 3,5-di-tert-butylsalicylic acid | 250 | Ti | 48 |
| Example 5 | 5-tert-octylsalicylic acid | 250 | Al | 27 |
| Example 6 | 3-methylsalicylic acid | 152 | Al | 27 |
| Example 7 | 3,5-di-tert-butylsalicylic acid | 250 | Al | 27 |
| Example 8 | 3,5-di-tert-butylsalicylic acid | 250 | Cr | 52 |
| Example 9 | 3-hydroxy-7-tert-butyl-2-naphthalenecarboxylic acid | 244 | Al | 27 |
| Example 10 | 2-hydroxy-7-tert-butyl-1-naphthalenecarboxylic acid | 244 | Al | 27 |
| Example 11 | 3-hydroxy-7-tert-octyl-2-naphthalenecarboxylic acid | 300 | Ti | 48 |
| Example 12 | 3,5-di-tert-butylsalicylic acid | 250 | Al | 27 |
| Example 13 | 3,5-di-tert-butylsalicylic acid | 250 | Al | 27 |

| Example No. | 2:1 type metal compound (Molecular weight) [D⟨COO, O⟩M H$^+$]$_2$ | | 3:2 type metal compound (Molecular weight) [D⟨COO, O⟩M$_2$]$_3$ | | 6:4 type metal compound (Molecular weight) [D⟨COO, O⟩M$_4$]$_6$ |
|---|---|---|---|---|---|
| Example 1 | 524 | Example Compound 1 | 798 | Example Compound 2 | 1596 |
| Example 2 | 549 | Example Compound 17 | 848 | Example Compound 18 | 1696 |
| Example 3 | 553 | Example Compound 35 | 856 | Example Compound 36 | 1712 |
| Example 4 | 545 | Example Compound 23 | 840 | Example Compound 24 | 1680 |
| Example 5 | 524 | Example Compound 7 | 798 | Example Compound 8 | 1596 |
| Example 6 | 328 | Example Compound 3 | 504 | Example Compound 4 | 1008 |
| Example 7 | 524 | Example Compound 1 | 798 | Example Compound 2 | 1596 |
| Example 8 | 549 | Example Compound 17 | 848 | Example Compound 18 | 1696 |
| Example 9 | 512 | Example Compound 9 | 780 | Example Compound 10 | 1560 |
| Example 10 | 512 | Example Compound 13 | 780 | Example Compound 14 | 1560 |
| Example 11 | 645 | Example Compound 29 | 990 | Example Compound 30 | 1980 |
| Example 12 | 524 | Example Compound 1 | 798 | Example Compound 2 | 1596 |
| Example 13 | 524 | Example Compound 1 | 798 | Example Compound 2 | 1596 |

Examples 14 through 25 relate to toners for developing electrostatic images containing a charge control agent of the present invention. In the description given below, figures for part(s) by weight are simply referred to as part(s).

Example 14

Styrene-acrylic copolymer resin [HIMER SMB600 (trade name), produced by Sanyo Kasei Co., Ltd.] . . . 100 parts Low polymer polypropylene [Biscal 550P (trade name), produced by Sanyo Kasei Co., Ltd.] . . . 2 parts Carbon Black [MA100 (trade name), produced by Mitsubishi Chemical Industries, Ltd.] . . . 5 parts Charge control agent (Example Product 1) . . . 2 parts The above ingredients were uniformly pre-mixed using a high-speed mixer, and then kneaded in a molten state using a heat roll, cooled, and roughly milled in a vibration mill. The obtained coarse product was finely pulverized using an air jet mill equipped with a classifier to yield a negatively chargeable toner 10 to 20 μm in particle size.

Five parts of this toner was admixed with 95 parts of an iron powder carrier [TEFV 200/300 (trade name), produced by Powdertech Co., Ltd.) to yield a developer.

The amount of initial blowoff charges of the developer was determined to be −20.5 μC/g. The amounts of initial blowoff charges of the developer under low-temperature low-humidity conditions and high-temperature high-humidity conditions were −20.2 μC/g and −19.8 μC/g, respectively, demonstrating very high stability; storage stability was also good.

When this toner was used for repeated cycles of actual imaging on a commercially available copying machine, high-quality images free of density reduction and fogging were obtained, with good charge stability and sustainability and no high-temperature offset phenomenon.

Example 15

A toner and developer according to the present invention were prepared and assessed in the same manner as in Example 14, except that the charge control agent used in Example 14 was replaced with Example Product 2. The amount of initial blowoff charges of the developer was determined to be −22.1 μC/g. The amounts of initial blowoff charges of the developer under low-temperature low-humidity conditions and high-temperature high-humidity conditions were −21.8 μC/g and −21.7 μC/g, respectively, demonstrating very high stability; storage stability was also good. When this toner was used for repeated cycles of actual imaging in the same manner as in Example 14, high-quality images free of density reduction and fogging were obtained, with good charge stability and sustainability and no high-temperature offset phenomenon.

Example 16

A toner and developer according to the present invention were prepared and assessed in the same manner as in Example 14, except that the charge control agent used in Example 14 was replaced with Example Product 3. The amount of initial blowoff charges of the developer was determined to be −20.2 μC/g. The amounts of initial blowoff charges of the developer under low-temperature low-humidity conditions and high-temperature high-humidity conditions were −19.8 μC/g and −19.5 μC/g, respectively, demonstrating very high stability; storage stability was also good. When this toner was used for repeated cycles of actual imaging in the same manner as in Example 14, high-quality images free of density reduction and fogging were obtained, with good charge stability and sustainability and no high-temperature offset phenomenon.

Example 17

A toner and developer according to the present invention were prepared and assessed in the same manner as in Example 14, except that the charge control agent used in Example 14 was replaced with Example Product 4. The amount of initial blowoff charges of the developer was determined to be −18.8 μC/g. The amounts of initial blowoff charges of the developer under low-temperature low-humidity conditions and high-temperature high-humidity conditions were −18.5 μC/g and −18.0 μC/g, respectively, demonstrating very high stability; storage stability was also good. When this toner was used for repeated cycles of actual imaging in the same manner as in Example 14, high-quality images free of density reduction and fogging were obtained, with good charge stability and sustainability and no high-temperature offset phenomenon.

Example 18

A toner and developer according to the present invention were prepared and assessed in the same manner as in Example 14, except that the charge control agent used in Example 14 was replaced with Example Product 9. The amount of initial blowoff charges of the developer was determined to be −18.3 μC/g. The amounts of initial blowoff charges of the developer under low-temperature low-humidity conditions and high-temperature high-humidity conditions were −17.9 μC/g and −17.7 μC/g, respectively, demonstrating very high stability; storage stability was also good. When this developer was used for repeated cycles of actual imaging in the same manner as in Example 14, high-quality images free of density reduction and fogging were obtained, with good charge stability and sustainability and no high-temperature offset phenomenon.

Example 19

A toner and developer according to the present invention were prepared and assessed in the same manner as in Example 14, except that the charge control agent used in Example 14 was replaced with Example Product 10. The amount of initial blowoff charges of the developer was determined to be −18.4 μC/g. The amounts of initial blowoff charges of the developer under low-temperature low-humidity conditions and high-temperature high-humidity conditions were −18.0 μC/g and −17.7 μC/g, respectively, demonstrating very high stability; storage stability was also good. When this toner was used for repeated cycles of actual imaging in the same manner as in Example 14, high-quality images free of density reduction and fogging were obtained, with good charge stability and sustainability and no high-temperature offset phenomenon.

Example 20

A toner and developer according to the present invention were prepared and assessed in the same manner as in Example 14, except that the charge control agent used in Example 14 was replaced with Example Product 11. The amount of initial blowoff charges of the developer was determined to be −18.0 μC/g. The amounts of initial blowoff charges of the developer under low-temperature low-humidity conditions and high-temperature high-humidity conditions were −17.7 μC/g and −17.5 μC/g, respectively, demonstrating very high stability; storage stability was also good. When this toner was used for repeated cycles of actual imaging in the same manner as in Example 14, high-quality images free of density reduction and fogging were obtained, with good charge stability and sustainability and no high-temperature offset phenomenon.

Example 21

A toner and developer according to the present invention were prepared and assessed in the same manner as in Example 14, except that the charge control agent used in Example 14 was replaced with Example Product 12. The amount of initial blowoff charges of the developer was determined to be −22.3 μC/g. The amounts of initial blowoff charges of the developer under low-temperature low-humidity conditions and high-temperature high-humidity conditions were −22.0 μC/g and −21.8 μC/g, respectively, demonstrating very high stability; storage stability was also good. When this developer was used for repeated cycles of actual imaging in the same manner as in Example 14, high-quality images free of density reduction and fogging were obtained, with good charge stability and sustainability and no high-temperature offset phenomenon.

Example 22

Polyester resin [HP-301 (trade name), produced by The Nippon Synthetic Chemical Industry, Co., Ltd.] . . . 100 parts Low polymer polypropylene [Biscal 550P (trade name), produced by Sanyo Kasei Co., Ltd.] . . . 2 parts Rhodamine dye [Oil Pink 312 (trade name), produced by Orient Chemical Industries Ltd.] . . . 3 parts Quinacridone Red . . . 3 parts Charge control agent (Example Product 1) . . . 2 parts The above ingredients were treated in the same manner as in Example 14 to yield a negatively chargeable magenta toner, which was then used to prepare a developer.

When this developer was used for repeated cycles of actual imaging, high-quality magenta images free of density reduction and fogging were obtained, with good charge stability and sustainability.

Example 23

Polyester resin [HP-301 (trade name), produced by The Nippon Synthetic Chemical Industry, Co., Ltd.] . . . 100 parts Low polymer polypropylene [Biscal 550P (trade name), produced by Sanyo Kasei Co., Ltd.] . . . 5 parts Phthalocyanine dye [Valifast Blue 2606 (trade name), produced by Orient Chemical Industries Ltd.] . . . 3 parts Charge control agent (Example Product 12) . . . 2 parts The above ingredients were treated in the same manner as in Example 14 to yield a negatively chargeable cyan toner, which was then used to prepare a developer.

When this developer was used for repeated cycles of actual imaging, high-quality cyan images free of density reduction and fogging were obtained, with good charge stability and sustainability.

Example 24

Polyester resin [HP-301 (trade name), produced by The Nippon Synthetic Chemical Industry, Co., Ltd.] . . . 100 parts Low polymer polypropylene [Biscal 550P (trade name), produced by Sanyo Kasei Co., Ltd.] . . . 2 parts Quinophthalone dye (C.I. Disperse Yellow 64) [Kayacelon Yellow E-3GL (trade name), produced by Nippon Kayaku Co., Ltd.] . . . 5 parts Charge control agent (Example Product 9) . . . 2 parts The above ingredients were treated in the same manner as in Example 14 to yield a negatively chargeable yellow toner, which was then used to prepare a developer.

When this developer was used for repeated cycles of actual imaging, high-quality yellow images free of density reduction and fogging were obtained, with good charge stability and sustainability.

Example 25

Styrene-acrylate copolymer resin [HIMER SMB600 (trade name), produced by Sanyo Kasei Co., Ltd.] . . . 100 parts Low polymer polypropylene [Biscal 550P (trade name), produced by Sanyo Kasei Co., Ltd.] . . . 8 parts Iron tetroxide [EPT-500 (trade name), produced by Toda Kogyo Corporation] . . . 50 parts Carbon black [MA-100, produced by Mitsubishi Chemical Industries, Ltd.] . . . 6 parts Charge control agent (Example Product 5) . . . 2 parts The above ingredients were uniformly pre-mixed using a ball mill to yield a premix, which was then kneaded in a molten state at 180° C. using a twin-screw extruder, cooled and thereafter roughly crushed, finely pulverized and classified to yield a one-component toner having a particle size of 5 to 15 μm.

When this toner was used for a commercial copying machine to form toner images, fog-free high-quality images with good thin-line reproducibility were obtained.

Examples 26 through 28 relate to powdery paints for electrostatic painting incorporating a charge control agent or charge enhancer of the present invention.

93 to 97.9 parts of a resin for powdery paint listed in Table 3, 2 parts of the charge control agent or charge enhancer of the present invention, and 0.1 to 5 parts of a coloring agent were uniformly pre-mixed using a ball mill, kneaded in a molten state using a heat roll, cooled, roughly pulverized and finely pulverized to yield a powdery paint for electrostatic painting having a particle size of 20 to 250 μm.

When the powdery paints for electrostatic painting thus obtained were subjected to an electrostatic painting test by the tribocharge method on a steel plate using an electrostatic powdery painting machine [Tribomatic (trade name), produced by Nordson K.K.], painted products having good appearance and no painting film defects were obtained at a paint adhesion efficiency of not less than 95%.

TABLE 3

| Example No. | Resin | Charge control agent or charge enhancer | Paint adhesion efficiency (%) |
|---|---|---|---|
| Example 26 | Acrylic resin | Example Product 1 | 97 |
| Example 27 | Acrylic resin | Example Product 2 | 96 |
| Example 28 | Polyester resin | Example Product 3 | 97 |

What is claimed is:

1. A 3:2 type metal compound of formula II:

wherein $R^1$, $R^2$, $R^3$ and $R^4$ independently represent a hydrogen, a linear or branched alkyl group, or a linear or branched unsaturated alkyl group; $R^1$ and $R^2$, $R^2$ and $R^3$, and $R^3$ and $R^4$ may bind together to form an aromatic or aliphatic ring which may have one or more substituents of a linear or branched alkyl group, or a linear or branched unsaturated alkyl group; and M is a trivalent metal.

2. Compound of claim 1 wherein M is a trivalent metal selected from the group consisting of Cr, Al, Ti, Fe, Ni, Co, Mn, Si and Sn.

3. A mixture of a 3:2 type compound of claim 1 with a 2:1 type metal compound of formula IV:

wherein $R^1$, $R^2$, $R^3$ and $R^4$ independently represent a hydrogen, a linear or branched alkyl group, or a linear or branched unsaturated alkyl group; $R^1$ and $R^2$, $R^2$ and $R^3$, and $R^3$ and $R^4$ may bind together to form an aromatic or aliphatic ring which may have one or more substituents of a linear or branched alkyl group, or a linear or branched unsaturated alkyl group; M is a metal; and $A^+$ is a cation.

4. A 6:4 type metal compound of formula III:

wherein $R^1$, $R^2$, $R^3$ and $R^4$ independently represent a hydrogen, a linear or branched alkyl group, or a linear or branched unsaturated alkyl group; $R^1$ and $R^2$, $R^2$ and $R^3$, and $R^3$ and $R^4$ may bind together to form an aromatic or aliphatic ring which may have one or more substituents of a linear or branched alkyl group, or a linear or branched unsaturated alkyl group; and M is a trivalent metal.

5. Compound of claim 4 wherein M is a trivalent metal selected from the group consisting of Cr, Al, Ti, Fe, Ni, Co, Mn, Si and Sn.

6. A mixture of a 6:4 type compound of claim 4 with a 2:1 type metal compound of formula IV:

wherein $R^1$, $R^2$, $R^3$ and $R^4$ independently represent a hydrogen, a linear or branched alkyl group, or a linear or branched unsaturated alkyl group; $R^1$ and $R^2$, $R^2$ and $R^3$, and $R^3$ and $R^4$ may bind together to form an aromatic or aliphatic ring which may have one or more substituents of a linear or branched alkyl group, or a linear or branched unsaturated alkyl group; M is a metal; and $A^+$ is a cation.

7. A mixture of claim 6 further including a 3:2 type metal compound of formula II:

wherein $R^1$, $R^2$, $R^3$ and $R^4$ independently represent a hydrogen, a linear or branched alkyl group, or a linear or branched unsaturated alkyl group; $R^1$ and $R^2$, $R^2$ and $R^3$, and $R^3$ and $R^4$ may bind together to form an aromatic or aliphatic ring which may have one or more substituents of a linear or branched alkyl group, or a linear or branched unsaturated alkyl group; and M is a trivalent metal.

* * * * *